(12) United States Patent
Jones et al.

(10) Patent No.: US 8,366,814 B2
(45) Date of Patent: Feb. 5, 2013

(54) GAS CHROMATOGRAPHY INLET LINER HAVING AT LEAST ONE INDICATOR

(75) Inventors: Brian A. Jones, State College, PA (US); Thomas E. Kane, Port Matilda, PA (US)

(73) Assignee: Restek Corporation, Bellefonte, PA (US)

( * ) Notice: Subject to any disclaimer, the term of this patent is extended or adjusted under 35 U.S.C. 154(b) by 228 days.

(21) Appl. No.: 12/660,241

(22) Filed: Feb. 23, 2010

(65) Prior Publication Data
US 2010/0282077 A1    Nov. 11, 2010

Related U.S. Application Data

(60) Provisional application No. 61/208,289, filed on Feb. 23, 2009.

(51) Int. Cl.
*B01D 53/02*    (2006.01)
(52) U.S. Cl. .................. 96/105; 96/417; 96/420; 95/89; 73/23.39; 73/23.41

(58) Field of Classification Search .................... 96/101, 96/105, 417, 418, 420; 95/82, 89; 73/23.35, 73/23.39, 23.41
See application file for complete search history.

(56) References Cited

U.S. PATENT DOCUMENTS

| | | | | |
|---|---|---|---|---|
| 4,035,168 A | * | 7/1977 | Jennings | 73/864.85 |
| 5,119,669 A | * | 6/1992 | Silvis et al. | 73/23.41 |
| 5,954,862 A | * | 9/1999 | Wilson | 96/101 |
| 6,093,371 A | * | 7/2000 | Wilson | 422/89 |
| 6,203,597 B1 | * | 3/2001 | Sasano et al. | 95/87 |
| 6,494,939 B1 | * | 12/2002 | Tipler | 96/105 |
| 6,498,042 B1 | * | 12/2002 | Wilson | 436/174 |
| 6,565,634 B1 | * | 5/2003 | van Egmond | 96/105 |
| 6,719,826 B2 | * | 4/2004 | Sasano et al. | 95/87 |
| 7,744,684 B2 | * | 6/2010 | Thomas | 96/417 |

* cited by examiner

*Primary Examiner* — Robert Clemente
(74) *Attorney, Agent, or Firm* — John F. A. Earley, III; Frank J. Bonini, Jr.; Harding, Earley, Follmer & Frailey, P.C.

(57) ABSTRACT

A gas chromatography inlet liner comprises a glass tube formed by a glass wall, the glass wall having pore channels formed therein, and an indicator present in the pore channels in at least part of the inlet liner. The indicator may be any element, compound, dopant, or mixture additive that modifies color or transparency of the inlet liner.

20 Claims, 5 Drawing Sheets

10

21
20

30

41
40

50

60

71
70

80

90

GAS CHROMATOGRAPHY INLET LINER HAVING AT LEAST ONE INDICATOR

CROSS-REFERENCE TO RELATED APPLICATIONS

This application claims the benefit under 35 U.S.C. Section 119(e) of prior filed provisional application No. 61/208,289 filed on Feb. 23, 2009, which is incorporated herein by reference.

BACKGROUND OF THE INVENTION

Gas chromatography (GC) is a well known analytical technique where gas phase mixtures are separated into their individual components and subsequently identified. The technique may be employed to obtain both qualitative and quantitative information about the components of the mixture. Specifically, the separation mechanism employs two different media, one moving (mobile phase) and one unmoving (stationary phase). In GC, the mobile phase is normally hydrogen or helium, which flows across the stationary phase, which is a solid or otherwise immobilized liquid on a solid support or the interior capillary wall.

The sample mixture is introduced into the mobile phase stream and the residence time of each component of the sample in the stationary phase relates to differences in their individual partitioning constants with respect to the two solvent phases.

Samples for GC are usually liquid and must be volatized prior to introduction to the mobile phase gas stream. GC analysis is typically divided into four stages:

1. sample preparation, where liquid samples are heated and volatilized,
2. sample introduction, where the sample vapor is loaded all or in part onto the analytical column,
3. separation, where the sample is separated into its individual components as it passes through the analytical column, and
4. detection, where the separated components are identified as they exit the analytical column.

In conventional GC instrumentation the first two steps are achieved in the sample inlet hardware. Inlet hardware often includes a replaceable sleeve, or liner. Liners are normally operated at elevated temperatures, e.g., over 200° C. This enhances the rate of sample vaporization and reduces adsorption on the inner surface of the liner [1]. Many internal configurations are available for liners, as well as coatings for them [2-12].

In most cases the configuration serves to enhance the degree of sample volatilization from the point of exit from the syringe needle to the column entrance, and provide gas phase sample homogeneity from components within the liquid mixture having different boiling points. A simple configuration for an inlet liner is a straight cylindrical tube of glass having a consistent inner diameter along the longitudinal path. Other configurations include more complex inner paths intended to increase turbulence, affect the comparatively short residence time the liquid sample is in the liner, or interrupt the liquid stream leaving the syringe needle. These internal configurations include tapers or goosenecks, baffles, funnels, inverted cup elements, spiral regions, points of flow constriction, and drilled holes along the longitudinal path of the liner.

Other elements of liners optionally include small plugs of packing materials such as glass wool [1], Carbofrit™ (Trademark of Restek Corporation) packing material, and more recently inert metal wire bundles [13] which serve as additional surface area sources for heat transfer into the sample and as a physical filter for any solid/nonvolatile contaminants present in the liquid sample.

During the injection process, it is also important to minimize sample/liner and (if applicable) sample/packing material interactions that can result in undesirable chemical reactions, decomposition, or permanent adsorption of the sample. It is equally important that the liner not contribute contaminants to the analysis, which may result in spurious peaks or an increase in the baseline signal in detection measurements of the components contained in the sample being analyzed.

In cases where liners become contaminated with solid/nonvolatile species it is necessary to replace them from time to time. Liner replacement frequency depends on the type of sample; with 'dirty' samples having high concentrations of high boiling point components or large amounts of nonvolatile particulate matrix shortening the service life of the liner.

Liners are manufactured from glass, primarily borosilicate, but also fused quartz, and less commonly from metal, mainly stainless steel [14].

Because of the techniques commonly employed in using a liner in a GC instrument it is often desirable for the liner to be transparent. It is particularly important to be able to see through the walls of these liners which contain packing material in order to ensure its proper plug position within the internal bore of the liner. It is also advantageous to be able to observe wool placement, and to be able to check for the presence of debris or other visual contaminants.

Various chemical coatings are applied to liners in order to reduce the degree of interaction between the sample and the surface of the liner. Sample-surface interactions may result in sample absorption in the coatings, decomposition of the coatings, and formation of new reaction products; in each case resulting in undesirable peaks (or loss of desirable ones) in detection measurements of the components contained in the sample being analyzed in the separation analysis. In addition to low sample-surface interactions, it is also desirable for the liner coating to be thermally stable in order to minimize background signal contributions originating from the liner coating itself detected by the analytical equipment. For glass substrate liners, common deactivation techniques include chemically treating the exposed silanol groups with organosilane reagents such as hexamethyldisilazane (HMDS), dimethyldichlorosilane (DMCS), and trimethylchlorosilane (TMCS) [15].

Another suitable coating is vapor deposited silicon, including the Siltek® Sulfinert® coatings [15-19]. This coating has been demonstrated on both borosilicate glass and metal surfaces, in both cases resulting in an opaque mirror finish whose color is dependant on the coating thickness.

Distinguishing liners from one supplier to another is largely dependant on printed markings or logos on the outer surface. Identifier marks have also been employed to describe liner orientation, lot number, part number, wool placement, etc. Common glass marking techniques include silk screen printing of enamels that are then baked onto the surface, controlled etching, or combinations of the two. The latter method suffers from poor contrast and hence visibility of the image is impaired, while the former introduces a chemically new surface with the potential of deleterious interactions with analytes. Deactivation processes optimized for silanol or glass surfaces can also yield bare areas or weakly bonded moieties that can exude contaminating volatiles into the flow stream at elevated temperatures. To be useful, suitable manufacturer liner identifiers in the practice of gas chromatography must be resistant to visual fading resulting from cycles to high temperature, and not interfere with the analysis, particularly by contributing gas phase contaminants into the sample analysis path.

One unique marking case is the Sulfinert™ (Trademark of Restek Corporation) process, which results in a fully deactivated and distinctive rainbow colored mirror finish which is readily recognizable, even at a distance During normal operation of GC instrumentation it is necessary to remove or replace one liner for another. Liners are routinely heated to over 200° C. during the sample analysis and may be removed and/or replaced between sample analysis runs. While GC instrument companies recommend first waiting for the instrument to completely cool, many users do not wait and remove liners from the system while they are still hot. This creates a safety risk for the operator because current liners are visually indistinguishable between hot or cooled states. This risk relates to all types of liners, both metal and glass.

Another weakness of the current technology relates to liners that have been previously used or subjected to high temperature. In many cases the deactivation coating may be compromised through excessive use or extended exposure of the liner to oxygen while hot. In these cases, the degree to which the coating contributes to the background signal of the analysis or loss of analytes due to adsorption or degradation is increased. In general, liners that have been used for prolonged periods behave more poorly than do new liners. In addition, dirty samples may leave residue behind in the liner that may impact future runs.

In some cases, sample residue may be visible as dark colored stains in the liner. In others, liners with compromised surfaces may appear clear and colorless. In addition, indications of residue are obscured while the liner is installed in the GC.

Discussion on Porous Glass

Two common methods of producing porous glasses are through sol-gel routes and from phase separation of high boron oxide containing borosilicate glasses, followed by acidic leaching. The latter method, commonly known as the Vycor process (Vycor is a trademark of Corning Glass Works) [20] allows for convenient fabrication of complex shapes using standard glass manufacturing equipment, and gives porous products of the same dimensions comprised of approximately 96% silicon dioxide when subjected to aqueous acid leaching. The pores can be blocked through high temperature sintering under vacuum with a significant amount of physical shrinkage, or by chemical means through internal deposition of polymers or other blocking agents. The polymers can be organic, inorganic, or combinations thereof. The siloxane-based polymers are of particular interest because of their convenient compatibility with glass surfaces and can be used in the preparation of composites with high thermal stability.

The degree of pore blockage can be tailored from partial to complete, depending on the nature of the chemistry and processes employed. For example, partial pore blocking with silicon dioxide precursors such as tetrachlorosilane, tetraethoxysilane and tetramethoxysilane can yield a channel structure that is highly selective toward hydrogen permeation over other gases of larger physical molecular size. [21-24].

Discussion on Doping and Dopants

Because the channels in porous Vycor and sol-gel produced glass can range from less than ten to hundreds of angstroms in diameter, they can be filled or doped with a wide variety of organic and inorganic materials. For example, small iron oxide particles can be synthesized within the pores through infusion of aqueous ferric nitrate solutions followed by thermal decomposition. Further modifications of the aggregates can be made by heating in a hydrogen atmosphere. [25] The restricted geometry inside the confined space within the pore can affect the spectral absorptive and fluorescence properties of the dopant chromophore [26]. See also [27]. Other metal ions and mixtures have also been used as dopants in porous glasses. [28-30].

Organic and organometallic compounds with useful optical and electronic properties have been used as dopants in porous Vycor glass [31-33].

Organic dyes have been infused into Vycor pores [34-36], Unblocked pores containing dopants have been used in gas sensing applications [37]. The dopants have also been encapsulated by organic polymers within these pores[38-42].

The mild conditions required for the creation of sol-gel glasses is compatible with a wide range of dopants that constitute the same family as those described above for infusion into porous Vycor glass. Because of a lack of interconnected pores, the chromophoric species are usually present during the gelation process. Further ripening of the gel can take place without damaging the entrained dyes, salts, or chromophoric particles [43-49].

Discussion on Thermochromic and Photochromic Dyes

Dyes that produce a color change with temperature are referred to as thermochromic and have been the subject of extensive study [50-56]. A number of chemical classes exhibiting this behavior have been reported, and include perylene dyes, encapsulated leucodyes, and some inorganic compounds. In addition, many photochromic compounds (those that change color on exposure to light at specific wavelengths) exhibit thermochromic behavior. Some examples of this class of compounds include spiropyrans, spiroxazines, and ethylene aromatics, and the color change is due to often reversible molecular rearrangements giving rise to differences in conjugation or ionic structure. Thermochromic and photochromic indicators have been introduced into both porous Vycor glass, and sol-gel glasses, with the polarity and geometric constraints in their vicinity affecting the stabilization of one isomeric form over another. Thus environmental effects can result in thermochromic or reverse thermochromic behavior with the same dye molecule. Encapsulation of the dyes within the pores of these inorganic glass matrices has been reported using polymethylmethacrylate to yield transparent composites with the anticipation that they could lead to the development of three-dimensional high density memory arrays [47].

The thermochromic effect can be gradual, with the color intensity varying with the percentage of dye molecules in each state. Photochromic images previously set through light exposure can sometimes be erased through thermochromic relaxation.

SUMMARY OF THE INVENTION

We present here a liner for gas chromatographic injection systems, which employs indicators within the glass substrate as a means to easily identify one liner from another. For the purpose of this disclosure the term indicator relates to any element, compound, dopant, or mixture additive to the glass substrate that modifies the native color or transparency of the glass substrate.

We further present here a liner which employs indicators as a means of visually identifying the thermal state of the liner.

We further present here a liner which employs indicators as a means of determining "use status", wherein it is possible to visually identify if the liner has been previously subjected to high temperature and optionally the duration of exposure beyond a specific threshold.

We further present here a liner which employs indicators with controlled physical placement as a means of identifying the orientation of the liner.

We further present here a liner which employs colored indicators that are visible under ordinary and/or ultraviolet light as a means of decoration, identification, or counterfeit detection.

In addition, we present a liner wherein the indicators are effectively blocked from surface interactions through thermally stable chemical capping.

We further present a liner which employs indicators receptive to photolithographic imaging.

DETAILED DESCRIPTION OF THE PREFERRED EMBODIMENTS

Figure 1A:
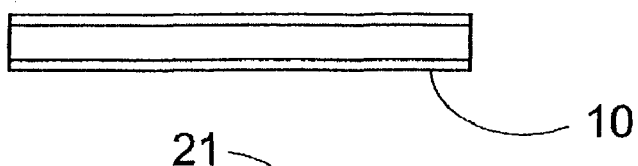
FIGS. 1A-1I are representations of several types of injection port liners known in the art.
Figure 1B:
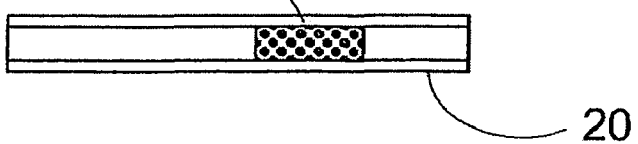
Figure 1C:
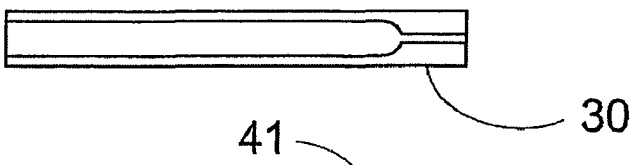
Figure 1D:
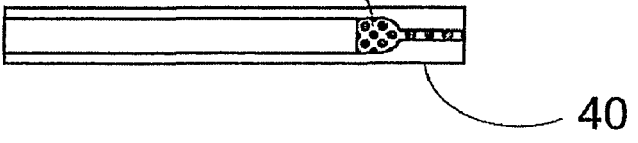
Figure 1E:
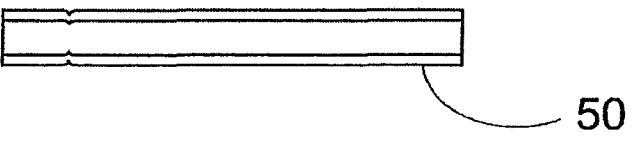
Figure 1F:
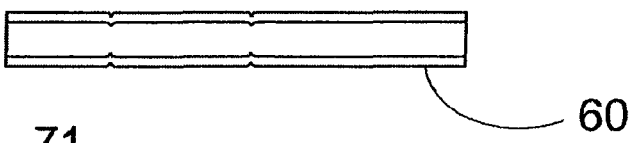
Figure 1G:
Figure 1H:
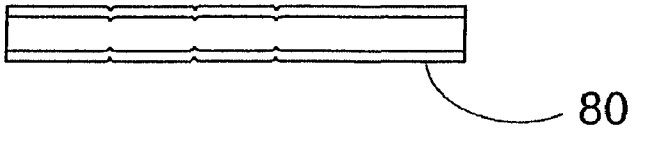
Figure 1I:

In FIGS. 1A-1I, sectional views of various sample inlet liner configurations known in the art are illustrated. FIG. 1A is an example of a straight through sample inlet liner 10. FIG. 1B illustrates a liner 20, comprising the liner 10 incorporating a matrix 21, which may be comprised of wool, particles, wire bundles, or other materials know in the art. FIG. 1C illustrates a single taper liner configuration 30, FIG. 1D illustrates a liner 40 having the same configuration as in liner 30, with the addition of a matrix 41, similar in composition to that designated as 21 in FIG. 1B. FIG. 1E illustrates a sample inlet liner 50 with dimples or constrictions extending into the inner bore. FIG. 1F illustrates a liner configuration 60 with two sets of internal dimples or constrictions; and FIG. 1G represents the same type of liner, with the same two sets of dimples or constrictions 70, but with the addition of a matrix 71 described above that is supported within the zone created by said dimples or constrictions. FIG. 1H illustrates a liner 80 having a straight through sample inlet liner with yet three sets of internal dimples or constrictions; and FIG. 1I illustrates a sample inlet liner 90 with multiple sets of interior baffles.

Figure 2:
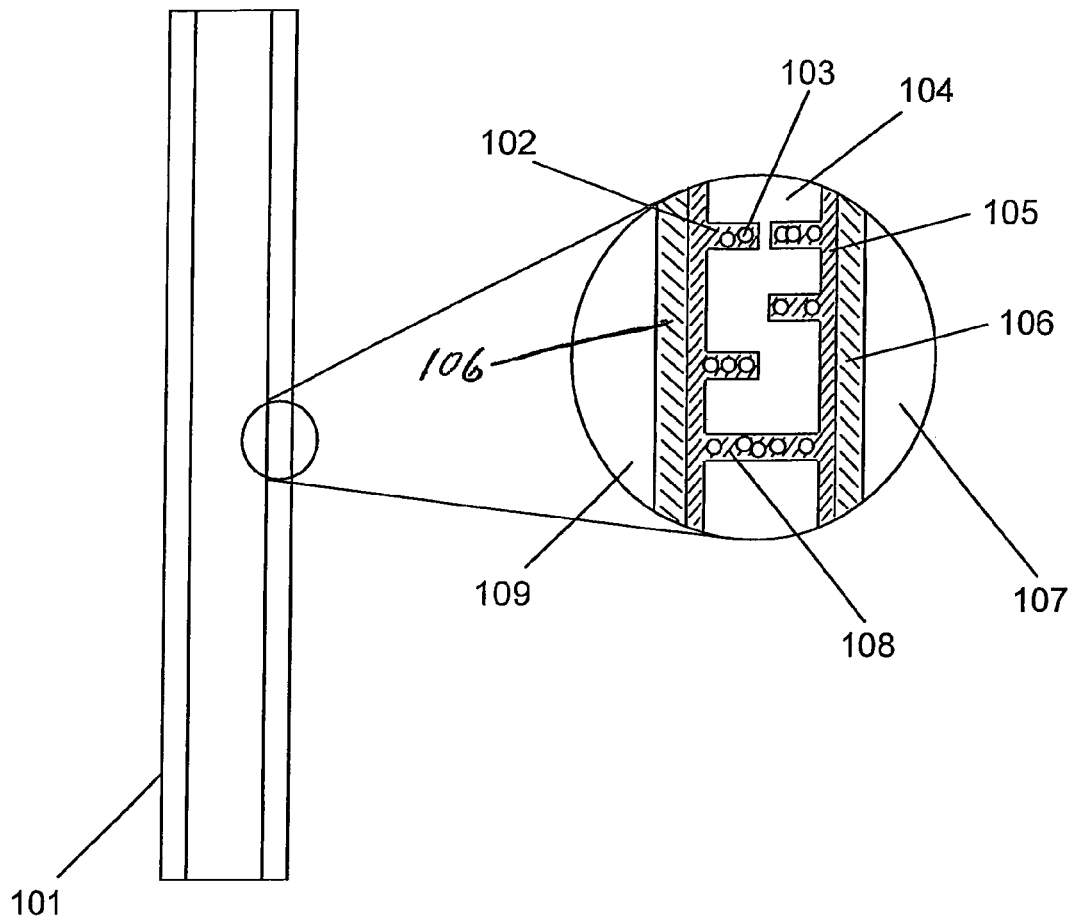
FIGS. 2 and 3 are representations of the preferred embodiments of a liner utilizing our invention that interfaces into a gas chromatograph injection port. The enlarged portions of the figures represent close-up views of the walls of the liners, showing the porous elements and dopant placement.

In FIG. 2, 101 is an example of the present invention and is fabricated from a porous glass.

In the enlarged view of a portion of this figure, 109 represents the inner region of the liner tube, with 107 being the outer.

102 represents a pore which may extend from the inner wall of the liner tube or the outer wall, but only penetrating part way through. 108 represents a pore channel with fluid connectivity between the inner and outer wall. It should be understood that the drawing is only a simplistic representation of the pore structure that in reality comprises random branching with some pathways extending completely through the glass structure, some looping back to the wall where pore origination first occurred, and some terminating within the glass matrix itself.

103 represents a dopant molecule that is capable of producing a visual effect that has been infused into the pores of the glass. 104 indicates the largely silicon dioxide support matrix that is interconnected and comprises the liner wall and structure. 108 illustrates an elevated temperature stable medium that surrounds the dopant domains and bonds to the pore walls, effectively eliminating carrier gas flow and entrained analytes penetrating deeply into and through the liner wall. Some of this pore-blocking material also coats the liner on both the inside and outside surfaces of the liner walls and is illustrated by 105. In order to eliminate absorptive activity towards analytes, the liner is coated with a final layer of a deactivant, that is usually silane or siloxane in nature, but may be comprised of other moieties as known in the art, and designated as 106.

Figure 3:
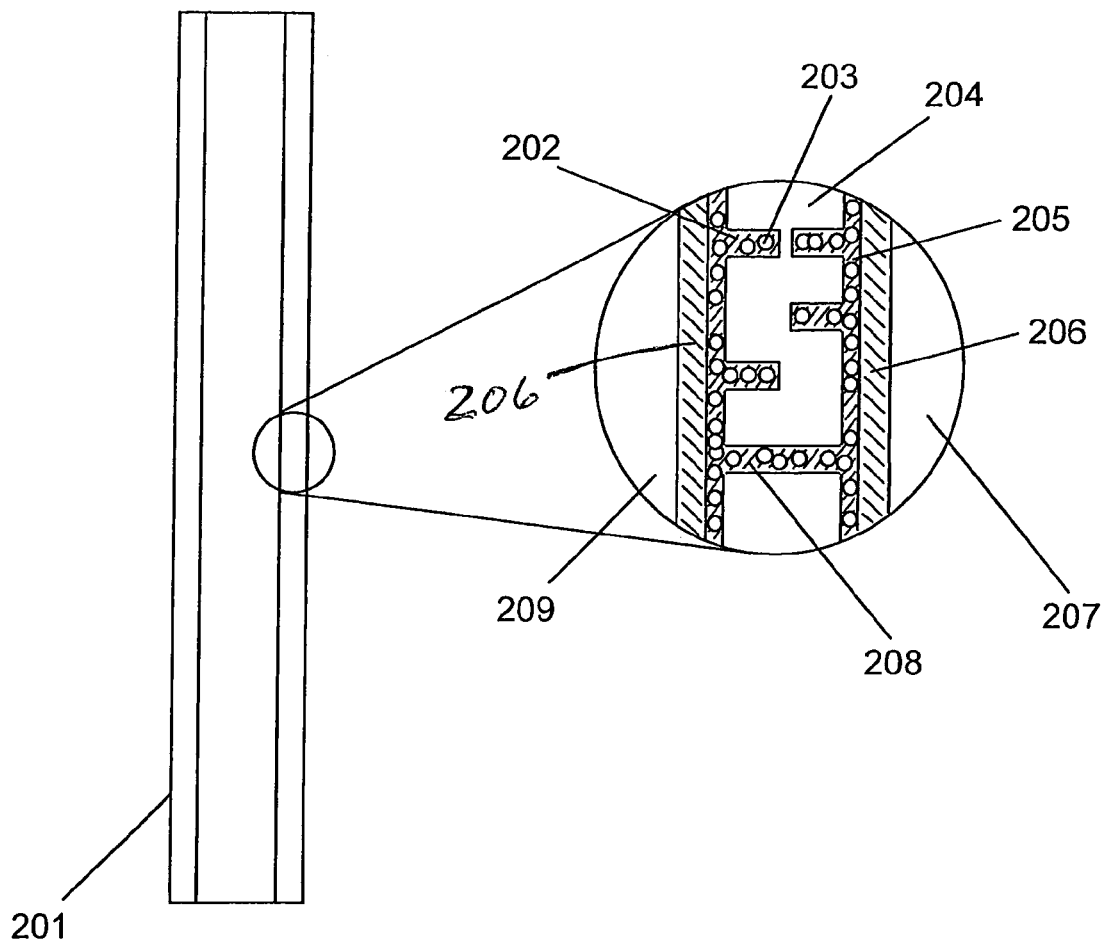

In FIG. 3, 201 is an example of the present invention and is fabricated from a porous glass. In the enlarged view of a portion of FIG. 3, 209 represents the inner region of the liner tube, with 207 being the outer. 202 represents a pore which may extend from the inner wall of the liner tube or the outer wall, but only penetrating part way through. 208 represents a pore channel with fluid connectivity between the inner and outer wall. It should be understood that this drawing also is only a simplistic representation of the pore structure that in reality comprises random branching with some pathways extending completely through the glass structure, some looping back to the wall where pore origination first occurred, and some terminating within the glass matrix itself. 203 represents a dopant molecule that is capable of producing a visual effect that has been infused into the pores of the glass. 204 indicates the largely silicon dioxide support matrix that is interconnected and comprises the liner wall and structure. 208 illustrates an elevated temperature stable medium that surrounds the dopant domains and bonds to the pore walls, effectively eliminating carrier gas flow and entrained analytes penetrating deeply into and through the liner wall. Some of this pore-blocking material also coats the liner on both the inside and outside surfaces of the liner walls and is illustrated by 205. In this Figure, the dopant is also present on the outer surface of the liner in abundance, and is represented in this form to show a co-deposition of the dopant and pore blocking material in a concerted step. The pore blocking media may be a sol-gel precursor that fills the initial pores of the glass, giving a reduction in their diameter and creating an internal medium with yet smaller pores. These can be further infused with additional dopants that may be the same or different to materials previously loaded in the pores. In order to eliminate absorptive activity towards analytes, the liner is coated with a final layer of a deactivant, that is usually silane or siloxane in nature, but may be comprised of other moieties as known in the art, and designated as here as 206.

The preferred material used in the embodiment of this invention is porous Vycor glass, with an average pore diameter preferably between 1000 and 1 nanometers, and preferably more between 100 and 1.5 nanometers, and most preferably between 10 and 2 nanometers. The dopants and or pore-blocking media can be admitted into the communicative pores of the substrate using a variety of techniques, including physical contact of solutions, with capillary forces wicking the medium inside; using simple diffusion, by placing the glass with pores already filled with liquid in physical contact with a new medium containing the desired material; or in the gas phase if the dopant or pore-blocking precursors are sufficiently volatile, with optional assistance by the application of elevated temperature and/or vacuum; by pressure differential between the inside and outside of the substrate wherein the reagents are carried through the pore channels by bulk flow of gases or liquids; and electro-driven, through application of an electric field, with the dopants and/or pore blocking media carrying an ionic charge, or through utilization of electroosmotic flow, with the direction and magnitude being influenced through beneficial application of solution pH.

The pore-filling operation may be complete, through total immersion in the influencing media, or may be partial through application of a stencil that only allows permeation through selected regions; through use of a temporary pore blocking agent, such as wax, that may be selectively applied initially, and then subsequently removed after treatment, rendering the now exposed surface suitable for additional chemical modification, reaction or doping; and through selective contact by a capillary or porous fiber in fluidic communication with the solution.

Superficially porous glass does not have the loading capacity for dyes and dopants to impart significant coloration to the body, so Pyrex-type glasses that have been acid leached are not suitable substrates for attaching them alone. In addition to complete removal of the boron-rich spinodal immiscible phase with aqueous acid in the Vycor process, a partial leaching technique on susceptible glasses may be employed to limit the extent of channel formation to a desired level. In some cases this may be targeted, such as where only a superficial level of doping of a dye with intense coloration may be required. In an analogous process, a non-porous glass liner may be coated with a sol-gel solution containing the desired dopants such that a relatively thin layer is produced. Multiple layers containing the same or different dopants can be built up through successive coatings.

For custom marking, laser writing techniques may be used to affect a color change in selected regions of the glass through irreversible decomposition of susceptible dopants, or through reversible means by selective excitation of suitable dye molecules through temporary rearrangement into forms exhibiting a different coloration.

Depending on the pore diameters, surface energies and the desired coating composition, supercritical drying may be an aid in processing to reduce the incidence of cracking. Coating films of low native surface tension that have this parameter sustained through the curing and drying processes appear to not require supercritical processing conditions.

A summary of exemplary visual effects and indicator classifications is shown below that is intended to be illuminating, but not limiting in any fashion.

Color, visible, based on light absorption
Color, visible, based on fluorescence
Color, invisible, except when illuminated with UV light based on fluorescence
Opacity or translucence based on light scattering
Change in color, visible, based on light absorption
Change in color, visible, based on fluorescence
Change in color, from at least one color (or colorless) to black, brown, or other dark color
Change in opacity, between transparent and opaque
Reversible transition
Irreversible transition
Use of receptive photochromic dopants that allow general or selective printing through photolithographic, photoflash or laser writing techniques that are optionally thermally erasable.

EXPERIMENTAL RESULTS

In each example following, pieces of porous Vycor 7930 28% pore volume and average pore diameter 4 nm were cut from 8 mm OD tubing and heated from room temperature to 140° C. at 5° C./min, and then held for 1 hour. They were then heated at approximately 10° C. per minute to 700° C. and held for 3 hours. The samples were transferred while hot into an airtight container and stored until ready for use.

Example 1

A piece of dried Vycor 7930 tubing was partially immersed for 10 seconds in a solution of 3.5 mg gold (III) chloride in 0.2 mL of water. The tubing was then removed from the solution and blotted dry with a tissue. The gold ion infused section of the tubing was a light yellow color. The tubing was then placed in an oven and heated at 5° C./min to 200° C. and immediately cooled. The portion of the tubing that had previously contacted the solution was a dark purple color, indicative of finely dispersed elemental gold within the pores of the glass. The remainder of the glass was colorless. The Merck Index reports the decomposition temperature of gold(III) chloride as 254° C.

Example 2

A piece of dried Vycor 7930 tubing was partially immersed for 10 seconds in a solution of 79.5 mg silver nitrate in 0.5 mL of water. The tubing was then removed from the solution and blotted dry with a tissue. The tubing was then placed in an oven and heated at 5° C./min and visually inspected at 100° C. intervals. The portion of the tubing that had previously contacted the solution was still colorless at 400° C., but turned a dark brown color after exposure to 500° C., followed by cooling, which is indicative of finely dispersed elemental silver within the pores of the glass. The remainder of the glass was colorless. The Merck Index reports the decomposition temperature of silver nitrate as 440° C.

Example 3

A piece of dried Vycor 7930 tubing was partially immersed for 10 seconds in a solution of 0.2 gm sucrose in 2 mL of water. The tubing was then removed from the solution and blotted dry with a tissue. The tubing was then placed in an oven and heated at 5° C./min to 200° C. and immediately cooled. The portion of the tubing that had previously contacted the sucrose solution was black in color, indicative of a carbonaceous decomposition residue within the pores of the glass. The remainder of the glass was colorless. The Merck Index reports the decomposition temperature of sucrose as 160-186° C.

Example 4

Approximately 10 mg of Trypan Blue was dissolved in 10 mL water. A piece of dried Vycor tubing was immersed in the solution and held for 1 hour. The tube was removed and blotted dry with a tissue. Very little coloration of the tube resulted, which may be attributed to the fact that this dye molecule is rather large in size, and likely is not able to penetrate deeply into the pores.

Example 5

Solvent Green 3 (3.9 mg) was dissolved in 15.5 mL of methylene chloride. A piece of dried Vycor tubing was immersed in the solution and held for 1 hour. The tube was removed and blotted dry with a tissue. It was very dark blue in color. The tube was dried to 200° C. in air and the coloration remained the same.

Example 6

A piece of dried Vycor was immersed in a solution of 1.0 mg of Methyl Orange in 10 mL water for 1 hour. The tube was removed and blotted dry with a tissue. It was a bright orange color. The tube was dried to 200° C. in air and the coloration remained the same.

Example 7

A solution of N,N'-ditridecyl-3,4,9,10-perylenetetracarboxylic diimide (0.3 mg) in 4.2 mL methylene chloride was prepared and a piece of Vycor tubing was immersed for 1 hour. Dye uptake appeared to be rapid, and a red fluorescent color resulted. The coloration appeared to exhibit thermochromic behavior as it became darker as the tube was heated to as high as 400° C., but returned to the same red fluorescent shade upon cooling.

Example 8

A solution of bianthrone (1.2 mg) in 183 μL of methylene chloride was prepared and a piece of dried Vycor was immersed in it for 1 hour. It as then removed and dried as above. The color was light yellow, which became darker on exposure to bright light. The color darkened irreversibly when heated to 300° C.

Example 9

A colorless solution of 1,3,3-trimethylindolino-8'-methoxybenzopyrylospiran (3.3 mg) in 4 mL of methylene chloride was prepared. On brief contact with dried Vycor tubing, an immediate rose/pink color appeared in the tubing which remained after drying to 200° C.

Example 10

A light pink solution of 1,3,3-trimethylindolino-beta-naphthopyrylospiran (1.1 mg) in 70 μL of methylene chloride was prepared. On brief contact with dried Vycor tubing an immediate dark red color resulted which remained after drying to 200° C.

Example 11

A piece of dried Vycor 7930 tubing was immersed in poly(dimethoxysiloxane) (Gelest PSI-026, containing 26.0-27.0% Si) until tiny bubbles stopped being evolved (3 hours). The tube was removed from the liquid, and the excess removed by blotting with a tissue. The glass was exposed to laboratory air and turned opaque within 30 minutes. Overnight exposure produced numerous large cracks within the tube, with several shards having been physically ejected from the main tube body.

Example 12

A piece of dried Vycor 7930 tubing was treated as in Example 11, but was immersed for 3 hours in water containing 2% HCl immediately after tissue blotting. The tube was rinsed with methanol and soaked in methanol overnight.

After removal from the methanol, the tube was immediately placed in a stainless steel vessel, which was pressurized to 2000 psi with $CO_2$. This vessel was heated to 250° C. while still under pressure, and then a vent was opened through a 20 cm piece of 30 μm ID fused silica tubing. During the venting, fresh $CO_2$ was admitted at 2000 psi at the opposing end of the vessel until 1 hour after liquid methanol ceased condensing at the fused silica tube outlet. The flow of fresh $CO_2$ was halted, and the pressure allowed to drop to ambient. The vessel was then allowed to cool to room temperature.

The tube was colorless and transparent after this treatment, with no cracks present. The process was repeated as above starting with soaking in poly(dimethoxysiloxane) through the supercritical $CO_2$ extraction. Again, no cracks were present.

The tube was placed in a muffle furnace and heated to 700° C. in air (held for 3 hours) to burn out residual carbon containing species. The tube exhibited an overall gain in mass after these treatments of 13.9%.

The purpose of this experiment was to verify that pore blocking had occurred by quantification of the increase in mass, and that supercritical drying could be successfully employed to maintain the structural integrity of the tube.

Example 13

A piece of Vycor tubing was immersed in a solution containing 10 mM ferric nitrate for 1 hour. It was then removed and blotted dry with a tissue. The glass was colorless. The tubing was then placed in an oven and heated at 5° C./min to 400° C. and held for 30 minutes. A uniform amber color developed throughout the glass. The iron oxide was converted into the gamma form by placing the tube in a stainless steel chamber, starting a hydrogen flow, and heating to 350° C. for 3 hours. The tube was removed from the chamber and heated in air to 400° C. to give a darker brown coloration, that became considerably lighter and more red after cooling to room temperature. This color change from dark to lighter/red was reversible with subsequent heating/cooling cycles.

A solution containing 25.5 gm 2-propanol, 1.5 gm water, 1.1 gm acetic acid, and 0.75 gm of bis-(trimethoxysilyl) ethane (BTSE) was allowed to stand 10 minutes, whereupon the tube was immersed in it for 10 seconds, removed, and the excess solution removed with a tissue. The tube was dried in a vacuum oven at 150° C. for 30 minutes. No cracking was present. The tube was again immersed in the BTSE solution above and dried again in the vacuum oven. This immersion/drying process was performed a third time. Again, no cracking was present, and the original BTSE solution never gelled during the entire experiment.

After the third BTSE treatment, the tube was heated at 5° C./min to 300° C. and held for 60 minutes in air. The intensity of the coloration was not diminished by this treatment.

Example 14

A piece of Vycor tubing was immersed in a solution containing 12.2 mg 3,4,9,10-perylenetetracarboxylic dianhydride and 86 mg sodium hydroxide in 10 ml of water for 1 hour. It was then removed and blotted dry with a tissue. The glass was a red color with some fluorescence. The tubing was then placed in an oven and heated at 5° C./min to 200° C. and held for 30 minutes. The tube was then immersed in a 1 M hydrochloric acid solution for 1 hour. The heating process to 200° C. was repeated to re-form the perylene dianhydride from the water soluble sodium salt form. After cooling, the bright colored tube was immersed in water overnight. No color leaching from the porous tube into the water occurred. [57, 58].

The tube was heated in air to 300° C. in a vessel intended to simulate the heating environment characteristic of an injection port assembly. Upon initial removal from the hot device, the tube had a dark brown coloration that became considerably lighter and more red during cooling to room temperature. This color change from dark to lighter/red was reversible with subsequent heating/cooling cycles.

Example 15

A piece of Vycor tubing was immersed in a solution containing 9 mg Rhodamine B in 2.99 gm methanol for 1 hour. It was then removed and blotted dry with a tissue. The glass was a bright fluorescent pink color. The tubing was then placed in an oven and heated at 5° C./min to 200° C. and held for 30 minutes. The bright pink color remained as before. The pores of the tube were blocked using a fresh activated solution of BTSE as in Example 13. After the third treatment, the tube was heated at 5° C./min to 300° C. and held for 60 minutes. The intensity of the coloration was not diminished by this treatment. [59].

The Rhodamine-doped tubing was then heated in a device intended to simulate an injection port assembly to 400° C. The heating was conducted in air to imitate the long term oxidation damage that could occur to a liner in a GC injection port with impure carrier gas or in the presence of atmospheric leaks. The tube was visually inspected over a period of 14 hours and the initial bright pink color slowly faded during this time to a very faint pink tint in an otherwise colorless tube.

Example 16

A piece of Vycor 7930 tubing was immersed in a solution of 18.0 gm cobalt chloride pentahydrate in 30.7 gm water for 1 hour. It was removed, rinsed briefly with water, and allowed to air dry overnight. It was then placed in a vacuum oven at 150° C. for 30 minutes to give an opaque blue coloration. Exposure to laboratory air produced a pink color after a few hours. The tube was treated with BTSE solution as in Example 13. It was then dried in a vacuum oven at 150° C. for 30 minutes to give a transparent blue coloration. No cracking was present.

This blue tube was immersed in water and it became pink after 60 seconds, showing some permeability of the silane coupling agent layer to water. The tube was dried again in the vacuum oven at 150° C. for 30 minutes to give a blue color again. The tube was again immersed in the BTSE solution above, dried again in the vacuum oven, and immersed in water as before. After this second treatment, the pink coloration only appeared after 10 minutes immersion. A third cycle of drying, BTSE solution immersion, drying, and water immersion gave no change from blue to pink, even after 1 week, indicating that the doped cobalt ions were no longer accessible for coordination by water.

Again, no cracking was present, and the original BTSE solution never gelled during the entire experiment.

Example 17

A piece of Vycor tubing was cut to 105 mm length and dried in air to 700° C. as described above. It was then immersed in a 100 mM solution of ferric nitrate to a depth of 45 mm and held for 2 minutes. The tube was then removed and allowed to drain onto an absorbent tissue. A faint coloration resulted in the doped area. The tube was placed in an oven and heated at 5° C./min to 400° C. and held for 30 minutes. A uniform amber color developed, but only in the doped region. The color turned lighter and more red as the temperature dropped to ambient. The opposite end of the tube was then immersed to 45 mm depth in the perylenetetracarboxylic dianhydride/sodium hydroxide solution in Example 7, and held for 5 minutes. The tube was then removed and allowed to drain vertically onto a tissue. The tubing was then placed in an oven and heated at 5° C./min to 200° C. and held for 30 minutes. The tube was then immersed to the 45 mm depth in a 1 M hydrochloric acid solution for 5 minutes, and then allowed to drain. The heating process to 200° C. was repeated to re-form the perylene dianhydride from the water soluble sodium salt form.

The tube was totally immersed in poly(dimethoxysiloxane) as in Example 11 and held for 3 hours, whereupon it was blotted dry with a tissue and then immediately immersed in water containing 10% formic acid, and allowed to stand overnight. The tube was then soaked in methanol for 3 hours. It was then subjected to supercritical drying as in Example 12. Instead of heating in a muffle furnace, the tube was treated with a second infusion of poly(dimethoxysiloxane) as above, with hydrolysis, methanol soaking and supercritical drying as before. The two separated colored zones were readily apparent, and both reversibly darkened from reddish to a brown color upon heating to 400° C., although with different shades. The tube was then deactivated using a proprietary gas phase process typical of other liners intended for use in gas chromatography.

Example 18

Figure 4:
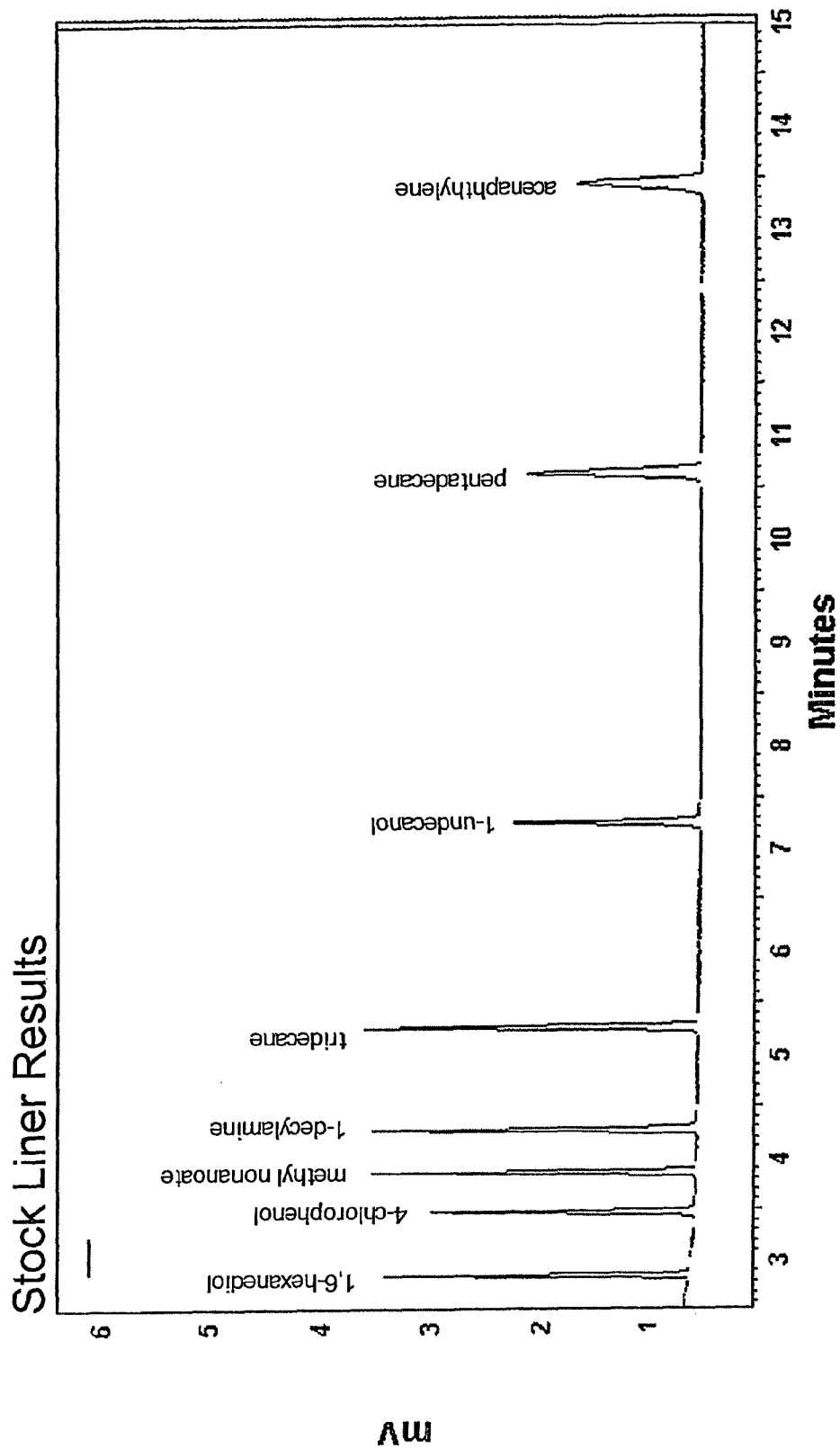
FIG. 4 is a graphical representation of a chromatogram generated of a chemical mixture using a deactivated injection port liner constructed according to the prior art and illustrated in FIG. 1.

A commercial straight-through deactivated liner of dimensions similar to the doped Vycor tube (Restek P/N: 20939) was installed in the injection port in a Thermo Trace 2000 Gas Chromatograph containing a 30 m, 0.25 mm, 0.25 µm Rxi-5MS column, and a flame ionization detector. Hydrogen was used as the carrier gas, and the inlet pressure was adjusted to give a reasonable linear velocity through the column. The injector was heated to 250° C., the oven to 125° C., and the detector to 320° C. After allowing for equilibration, 1 µL of a 500 ppm Rxi Test Mix (Restek P/N: 35247, containing 1,6-hexanediol, 4-chlorophenol, methyl nonanoate, 1-decylamine, tridecane, 1-undecanol, pentadecane and acenaphthylene, and listed in typical elution order) was injected into the system. The chromatogram illustrated in FIG. 4 was produced.

Figure 5:
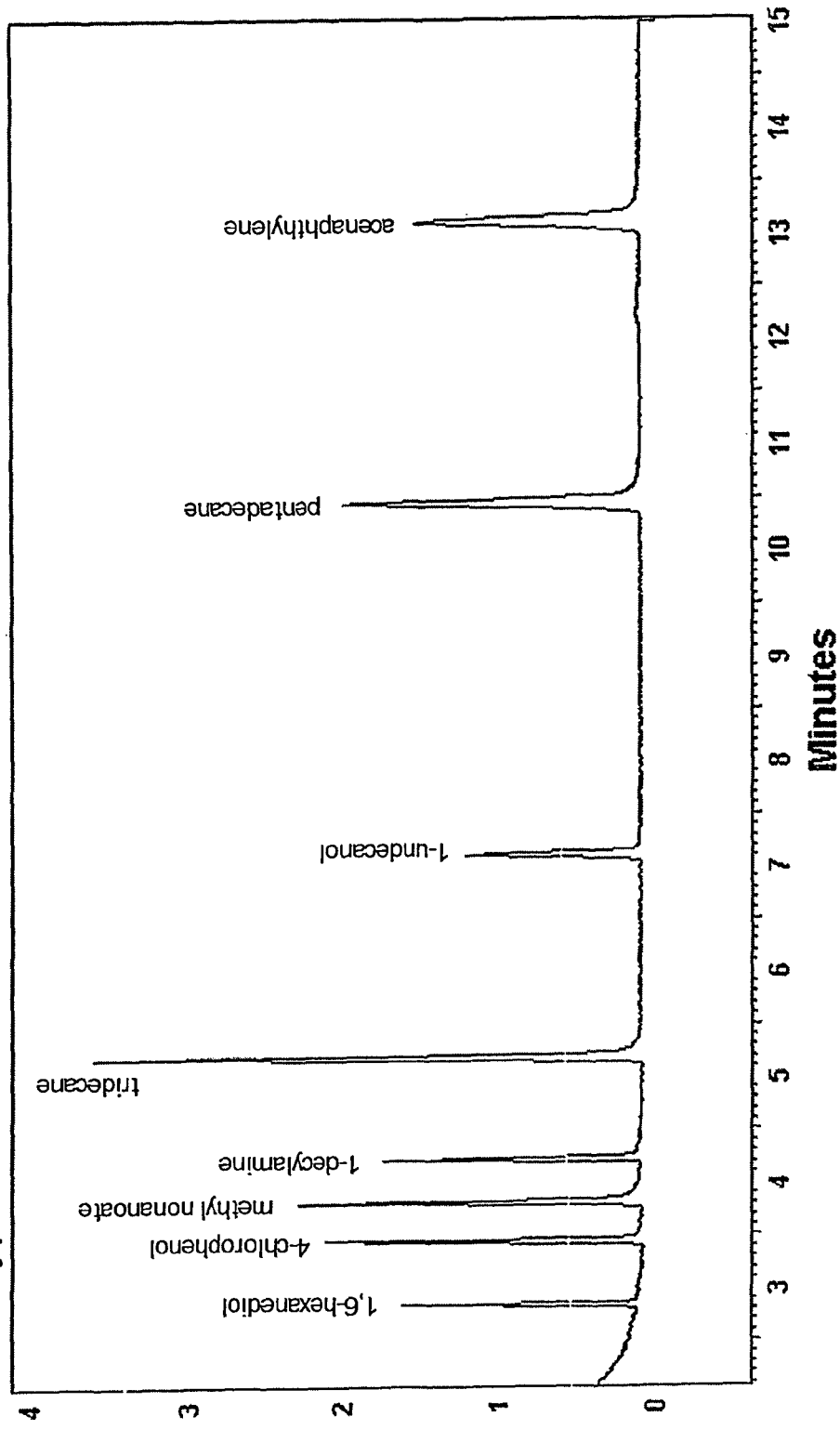
FIG. 5 is a graphical representation of a chromatogram generated of a chemical mixture using a deactivated injection port liner constructed according to the preferred embodiments of this invention and illustrated in FIG. 2.

The injector was cooled and the liner replaced with the doped Vycor tube from Example 17. After re-equilibration of the heated zones, the test sample was analyzed as before, producing the chromatogram illustrated in FIG. 5. The asymmetry of the active components, specifically the diol, phenol, amine, and alcohol is excellent, indicating adequate deactivation/blocking of silanol groups on the Vycor liner surfaces.

Example 19

A solution of anthracene in pentane was prepared at a concentration of 1 mg/mL. Some of the liquid was absorbed onto a porous cellulose bundle, which was used to inscribe lettering onto a piece of Vycor tubing. No visual indication of the writing was apparent, except when illuminated with ultraviolet light, whereupon the blue fluorescing image became evident.

Example 20

A piece of Vycor tubing was immersed at one end in a solution containing 10 mM ferric nitrate to a depth of 0.25 inches and held for 2 minutes. It was then removed and the excess solution was carefully blotted with a tissue. The tube was then heated and processed as in Example 13 above to develop the thermochromic iron oxide coloration which allowed for easy confirmation of the orientation of the tube at the time of immersion.

To prevent users from touching an inlet liner installed in the GC sample inlet hardware while the inlet liner is still hot, an inlet liner of the invention having a reversible thermochromic indicator present in at least part of the inlet liner may be used. An example of such an inlet liner is disclosed in Example 7. Accordingly, because there is a difference in color with the reversible thermochromic indicator between when it is at room temperature and when it is hot, users may avoid being burned by not touching the inlet liner when they observe that a color change has occurred in the inlet liner indicating that the inlet liner is hot, and waiting until when the inlet liner has cooled by observing a reversal of the color change.

The invention also may be used to show when an inlet liner has reached the end of its useful life and should be replaced. For example, an inlet liner of the invention having a indicator present in at least part of the inlet liner that is reactive to oxygen may be used to indicate when the inlet liner has suffered long term oxidation damage and should be replace. An example of such an inlet liner is disclosed in Example 15, where a fading of the color of the inventive inlet liner over the duration of its use is indicative of oxidation damage to the inlet tube.

The invention also may be used to show when our inlet liner has been previously subjected to a high temperature, and may need to be replaced. For example, an inlet liner of the invention having an irreversible thermochromic indicator present in at least part of the inlet liner may be used to show when the inlet liner has been subjected to a temperature above a particular temperature (e.g., a high temperature) by looking to see if an irreversible color change has taken place in the inventive inlet liner, in which the indicator used in the inlet liner irreversibly changes color when subject to temperatures above the particular temperature (e.g., a high temperature).

The invention also may be used to determine proper orientation of the inlet liner so that the inlet liner is correctly oriented when installed in the GC sample inlet hardware. For example, an inlet liner of the invention having an indicator positioned therein only at one end of the inlet liner or only at a portion of one end portion of the inlet liner may be used to distinguish between an inlet end of the inlet liner and an outlet end of the inlet liner.

Further, in accordance with the invention, an inlet liner may employ colored indicators that are visible under ordinary and/or ultraviolet light for decoration, identification, and/or counterfeit detection purposes. For example, an inlet liner may be provided with a colored indicator positioned in the pore channels in at least part of the inlet liner to decorate the inlet liner, and/or to mark the inlet liner with a symbol, design, or trademark to identify the inlet liner and distinguish it from a competitor's product, and/or to mark the inlet liner with a symbol, design, or marking, preferably one visible only under ultraviolet light, to show that the marked inlet liner is genuine and not counterfeit.

The references referred to in this application and listed below are hereby incorporated herein by reference.

REFERENCES

1. Konrad Grob in "Split and Splitless Injection for Quantitative Gas Chromatography, 4$^{th}$ Ed., Wiley-VCH, 2001.
2. *Anal. Chem.* 2002, 74, 10-16 "The Two Options for Sample Evaporation in Hot GC Injectors: Thermospray and Band Formation. Optimization of Conditions and Injector Design" Koni Grob and Maurus Biedermann.
3. U.S. Pat. No. 5,954,862 "Sample Inlet Liner" William H. Wilson.
4. U.S. Pat. No. 5,472,670 "Gas Chromatography Sample Injector And Apparatus Using Same" Peter de B. Harrington and Hans P. Whittenberg.
5. U.S. Pat. No. 5,119,669 "Sleeve Units for Inlet Splitters of Capillary Gas Chromatographs" Paul H. Silvis.
6. U.S. Pat. No. 6,565,634 "Injection Liner" Wil van Egmond.
7. U.S. Pat. No. 6,719,826 "Method and Apparatus for Sample Injecting in Gas Chromatography" Ryoichi Sasano, Motoaki Satoh, and Yutaka Nakanishi.
8. U.S. Pat. No. 6,498,042 "PTFE Matrix in a Sample Inlet Liner and Method of Use" William H. Wilson.
9. U.S. Pat. No. 4,035,168 "Nonreactive Inlet Splitter for Gas Chromatography and Method" Walter G. Jennings.
10. U.S. Pat. No. 5,997,615 "Large-Sample Accessory for a Gas Chromatograph" Huan V. Luong, Hsing Kuang Lin, Howard Fruwirth, George S. Mueller.
11. U.S. Pat. No. 6,203,597 "Method and Apparatus for Mass Injection of Sample" Ryoichi Sasano, Kazuhiko Yamazaki, Masahiro Furuno.
12. U.S. Pat. No. 6,494,939 "Zero-Dilution Split Injector Liner Gas Chromatography" Andrew Tipler.
13. U.S. patent application Ser. No. 12/157,202, Paul H. Silvis and Thomas E. Kane, Restek Corporation, patent pending.
14. For example, Catalog #s: 20726, 20974, 21700, and 21702 in the 2009 Restek Corporation Product Catalog.
15. "A Guide To Gas Chromatography", W. Rodel and G. Wolm, Huthig Verlag, GmbH, Heidelberg, Germany.
16. U.S. Pat. No. 6,511,760 "Method of Passivating a Gas Vessel or Component of a Gas Transfer System Using a Silicon Overlay Coating" Gary A. Barone, Andy S. Schuyler, and Joseph Stauffer.
17. U.S. Pat. No. 7,070,833 "Method for Chemical Vapor Deposition of Silicon on to Substrates for Use in Corrosive and Vacuum Environments" David A. Smith, Gary A. Barone, Martin E. Higgins, Bruce R. F. Kendall, and David J. Lavrich.
18. US Patent Appl. 2009/0029178 "Process for the Modification of Substrate Surfaces Through the Deposition of Amorphous Silicon Layers Followed by Surface Functionalization with Organic Molecules and Functionalized Structures" David A. Smith, Gary A. Barone, and Martin E. Higgins.
19. Restek Corporation 2009 Catalog.
20. U.S. Pat. No. 2,106,744 "Treated Borosilicate Glass" H. Hood, M Nordberg.
21. M. Tsapatsis and G. Gavalas "Structure And Aging Characteristics Of H2-Permselective SiO2-Vycor Membranes, *J. Membrane Science,* 87, 281-296, (1994).
22. *J. Mater. Res.*, Vol. 11, No. 12, December 1996, 3164-3173 "Microporous SiO2-Vycor membranes for gas separation" R. A. Levy, E. S. Ramos, L. N. Krasnoperov, A. Datta, and J. M. Grow.
23. *Journal of Membrane Science* 210 (2002) 291-306 "Gas Permeation Characteristics Of A Hydrogen Selective Supported Silica Membrane" Doohwan Lee, S. Ted Oyama.
24. *Journal of Colloid and Interface Science* 314 (2007) 589-603 "Inorganic Membranes For Hydrogen Production And Purification: A Critical Review And Perspective" G. Q. Lu, J. C. Diniz da Costa, M. Duke, S. Giessler, R. Socolow, R. H. Williams, T. Kreutz.

25. *JETP Letters*, 2006, Vol. 83, No. 7, pp. 298-301 "Diffraction Studies of the Crystalline and Magnetic Structures of gamma-Fe2O3 Iron Oxide Nanostructured in Porous Glass" I. V. Golosovsky, M. Tovar, U. Hoffman, I. Mirebeau, F. Fauth, A. Kurdyukov, and Yu. A. Kumzerov.
26. *Journal of Molecular Catalysis A: Chemical* 155 2000. 143-153 "Control of bandgap of iron oxide through its encapsulation into SiO-based mesoporous materials" Masakazu Iwamoto, Takayuki Abe, Yukio Tachibana.
27. *Journal of Non-Crystalline Solids* 319 (2003) 154-162 "Iron and iron oxide particle growth in porous Vycor glass; correlation with optical and magnetic properties" D. Sunil, H. D. Gafney, M. H. Rafailovich, J. Sokolov, R. J. Gambino, D. M. Huang.
28. U.S. Pat. No. 6,211,526 "Marking of Materials Using Luminescent and Optically Stimulable Glasses" A. L. Huston, B. L. Justus.
29. *J. Phys. Chem.* 1985, 89, 2120-2122 "Photophysical Properties of Cadmium Sulfide Deposited in Porous Vycor Glass" J. Kuczynski and J. K. Thomas.
30. *Applied Physics Letters* 88, 103110 (2006) "Study of Porous Glass Doped With Quantum Dots or Laser Dyes Under Alpha Irradiation" S. E. Létant and T.-F. Wang.
31. *Solar Energy Materials* 8 (1983) 399-409 "Transparent High Surface Area Porous Supports as New Materials for Luminescent Solar Concentrators" R. Reisfeld, N. Manor, and D. Avnir.
32. *Spectroscopy Lett.* 21(2) 1988 127-145 "Vycor Porous Glass (Thirsty Glass) as a Reaction Medium for Optical Waveguide Based Chemical Vapor Detectors" T. J. Novak and R. A. Mackay.
33. *Journal of Non-Crystalline Solids* 319 (2003) 163-173 "Effect of the Photodeposition of Tin on the Consolidation of Porous Vycor Glass" Jinquan Dong, Dehipawalage Sunil, Harry D. Gafney, Steven A. Schwarz.
34. *Journal of Non-Crystalline Solids* 74 (1985) 395-406 "Organic Fluorescent Dyes Trapped In Silica And Silica-Titania Thin Films By The Sol-Gel Method. Photophysical, Film And Cage Properties" David Avnir, Vered R. Kaufman And Renata Reisfeld.
35. *Appl. Phys. Lett.* 67, 3703 (1995) "Two-photon Pumped Cavity Lasing in Novel Dye Doped Bulk Matrix Rods" Guang S. He, Chan F. Zhao, Jayant D. Bhawalkar, and Paras N. Prasad.
36. *Physical Review Letters*, Volume 56, Issue 2, Jan. 13, 1986, pp. 197-200 "Self-Diffusion of a Molecule in Porous Vycor Glass" W. D. Dozier, J. M. Drake, and J. Klafter.
37. U.S. Pat. No. 7,364,700 "Ozone Gas Sensing Element Detection Apparatus, and Measurement Method" Yasuko Maruo, Shigeo Ogawa, and Seizou Sakata, Tohru Tanaka.
38. U.S. Pat. No. 6,402,037 "Two-Photon Upconverting Dyes and Applications" Paras N. Prasad, Jayant D. Bhawalker, Ping Chin Cheng, Shan Jen Pan.
39. US Patent Appl. 2006/0194122 "Hologram Recording Material and Optical Recording Medium" Hiroo Takizawa.
40. U.S. Pat. No. 7,232,637 "Light Sensitive Media for Optical Devices Using Organic Mesophasic Materials" Michael C. Cole, Timothy J. Trentler.
41. *Microporous and Mesoporous Materials* 60 (2003) 19-30 "Porous glasses in the 21st century—a short review" D. Enke, F. Janowski, W. Schwieger.
42. U.S. Pat. No. 4,878,224 "Dye Lasers" James E. Kuder, James L. McGinnis, Harris A. Goldberg, Timothy R. Hart, Tessie M. Che.
43. *Journal of Sol-Gel Science and Technology*, 2, 81-86 (1994) "Structures and Properties of Ormosils" John D. Mackenzie.
44. *Khimiya Geterotsiklicheskikh Soedinenii*, No. 4, pp. 435-459, April, 1979. "Synthesis and Properties of Spiropyrans That are Capable of Reversible Opening of the Pyran Ring (Review)" E. R. Zakhs, V. M. Martynova, and L. S. Efros.
45. *Acc. Chem. Res.*, 1995, 28 (8), 328-334 "Organic Chemistry within Ceramic Matrixes: Doped Sol-Gel Materials" David Avnir.
46. *Applied Spectroscopy*, 53(7), 1999 785-791 "Reduction of Indicator Leaching from Doped Sol-Gels by Attachment of Macromolecular Carriers" Peter J. Skrdla, S. Scott Saavedra, and Neal R. Armstrong.
47. *Journal of Non-Crystalline Solids* 113 (1989) 137-145 "Applications Of The Sol-Gel Process For The Preparation Of Photochromic Information-Recording Materials: Synthesis, Properties, Mechanisms" David Levy, Shlomo Einhorn and David Avnir.
48. WO 2008/028128 "LIGAND EXCHANGE THERMOCHROMIC, (LETC), SYSTEMS" Vander Griend, Douglas, A.; Ogburn, Paul, H., Jr.; Millett, Frederick, A.; Millett, Frederick, C.; Winkle, Derick, D.; Byker, Harlan, J.; Veldkamp, Brad, S.
49. *Chem. Mater.*, 1997, 9 (12), 2666-2670 "Photochromic Sol-Gel Materials" David Levy.
50. "Chromic Phenomena-Technological Applications of Colour Chemistry" ed. P. Bamfield, Published by The Royal Society of Chemistry, Thomas Graham House, Science Park, Milton Road, Cambridge.
51. U.S. Pat. No. 4,344,909 "Thermochromic Composition" F. J. A. M. C. De Blauwe.
52. *Chem. Rev.*, 1968, 68 (6), 649-657 "Thermochromism of Inorganic Compounds" Jesse H. Day.
53. U.S. Pat. No. 6,890,377 "Thermochromatic Rylene Dyes" A. Bohm, M. Krieger, S. Becker, K. Mullen.
54. *Chem. Rev.*, 2004, 104 (5), 2751-2776 "Photo-, Thermo-, Solvato-, and Electrochromic Spiroheterocyclic Compounds" Vladimir I. Minkin.
55. U.S. Pat. No. 7,304,008 "Thermochromic Material" A. V. Belykh, A. M. Efremov, M. D. Mikhailov.
56. *Chem. Rev.*, 2000, 100 (5), 1817-1846 "Linear and Nonlinear Optical Properties of Photochromic Molecules and Materials" Jacques A. Delaire, and Keitaro Nakatani.
57. *J. Mater. Chem.*, 2008, 18, 5615-5624 "Post-modification of helical dipeptido polyisocyanides using the 'click' reaction" Heather J. Kitto, Erik Schwartz, Marlies Nijemeisland, Matthieu Koepf, Jeroen J. L. M. Cornelissen, Alan E. Rowan and Roeland J. M. Nolte.
58. *Org. Biomol. Chem.*, 2005, 3, 1708-1713 "Optical glucose detection across the visible spectrum using anionic fluorescent dyes and a viologen quencher in a two-component saccharide sensing system" David B. Cordes, Aaron Miller, Soya Gamsey, Zach Sharrett, Praveen Thoniyot, Ritchie Wessling and Bakthan Singaram.
59. *J. Am. Ceram. Soc.*, 88 [12] 3458-3468 (2005) "Synthesis of Rhodamine B-Doped and Monodispersed Spherical Particles of Polyorganosiloxane Using a W/O Emulsion" Taichi Matsumoto, Yasushi Takayama, Hiroaki Onoda, and Kazuo Kojimaw, Noriyuki Wada.

What is claimed is:
1. A gas chromatography inlet liner, comprising
a glass tube formed by a glass wall,
the glass wall having pore channels formed therein, and
an indicator present in the pore channels in at least part of the inlet liner.

2. The inlet liner of claim 1,
the indicator being a thermochromic dye.

3. The inlet liner of claim 1,
the indicator being a photochromic dye.

4. The inlet liner of claim 1,
the indicator being an element, compound, dopant, or mixture additive that modifies color or transparency of the inlet liner.

5. The inlet liner of claim 1,
wherein a change in temperature of the indicator causes an irreversible change in the indicator.

6. The inlet liner of claim 1,
wherein a change in temperature of the indicator causes a reversible change in the indicator.

7. The inlet liner of claim 1,
wherein a change in temperature of the indicator causes a change in the indicator, the change in the indicator being exhibited as a spectral shift change or change in light absorbance in at least part of the inlet liner.

8. The inlet liner of claim 1,
wherein a change in temperature of the indicator causes a change in the indicator, the change in the indicator being exhibited as a change in degree of transmittance of light through the glass wall in at least part of the inlet liner.

9. The inlet liner of claim 1,
wherein a change in temperature of the indicator causes a change in the indicator, the change in the indicator being exhibited as a change in the indicator being exhibited as a change in color in at least part of the inlet liner.

10. The inlet liner of claim 1, wherein the indicator is thermochromic.

11. The inlet liner of claim 1, wherein the indicator is fluorescent.

12. The inlet liner of claim 1, wherein the indicator is permanently colored and remains unchanged through multiple thermal cycles.

13. The inlet liner of claim 1, wherein the inlet liner is deactivated with silanes.

14. The inlet liner of claim 1, wherein the indicator has a color intensity that decays over time in response to thermal or oxidative stresses.

15. The inlet liner of claim 1, wherein the indicator is photochromic.

16. The inlet liner of claim 15, wherein the photochromic indicator is converted to a colored form through exposure to light of a particular frequency range.

17. The inlet liner of claim 16, wherein the conversion to a colored form is in selected regions of the substrate, through photolithographic or focused exposure means.

18. The inlet liner of claim 15, wherein the photochromic effect is thermally erasable.

19. The inlet liner of claim 1, wherein the indicator is only visible under ultraviolet light.

20. The inlet liner of claim 1, further including
a chromatographically compatible sealant for sealing the pore channels containing the indicator.

* * * * *